United States Patent [19]

Grosch et al.

[11] Patent Number: 4,673,638

[45] Date of Patent: Jun. 16, 1987

[54] METHOD FOR DETECTION AND ISOLATION OF A MICROORGANISM

[75] Inventors: Josephine Grosch; Gary A. Wilson, both of Elkhart; Karen Wollweber, South Bend; Clifford O. Yehle, Elkhart, all of Ind.

[73] Assignee: Miles Laboratories, Inc., Elkhart, Ind.

[21] Appl. No.: 721,329

[22] Filed: Apr. 9, 1985

Related U.S. Application Data

[63] Continuation of Ser. No. 438,542, Nov. 1, 1982, abandoned.

[51] Int. Cl.$^4$ .............................................. C12Q 1/04
[52] U.S. Cl. ........................................ 435/34; 435/30; 435/38
[58] Field of Search ................... 435/30, 31, 32, 33, 435/34, 36, 37, 38, 39, 40

[56] References Cited

U.S. PATENT DOCUMENTS

| | | | |
|---|---|---|---|
| 3,929,583 | 12/1975 | Sharpe et al. | 435/301 |
| 4,237,223 | 12/1980 | Metz | 435/30 |
| 4,397,955 | 8/1983 | Entis et al. | 435/30 |
| 4,421,849 | 12/1983 | Breuker | 435/33 |

OTHER PUBLICATIONS

Manual of Clinical Microbiology, 3rd Edition, (1980), pp. 1003–1004.

*Primary Examiner*—David M. Naff
*Assistant Examiner*—William J. Herald
*Attorney, Agent, or Firm*—Edward P. Gray

[57] ABSTRACT

A method is provided for detecting a microorganism which produces a desired substance. The method involves overlaying a membrane on an agar surface in a predetermined orientation. Microorganisms are grown on the membrane and the substance allowed to pass into the agar. The membrane is removed and a detectable reaction between the substance and one or more reagents is observed. The location of the microorganism to be detected can be determined by the predetermined orientation, and the microorganism can be isolated by removing it from the membrane. When the substance is not secreted by the microorganism, the microorganisms are lysed releasing the substance for passage into the agar. The microorganisms producing the substance can be located on replicate plates and isolated.

4 Claims, No Drawings

METHOD FOR DETECTION AND ISOLATION OF A MICROORGANISM

This is a continuation of application Ser. No. 438,542, filed Nov. 1, 1982, now abandoned.

BACKGROUND OF THE INVENTION

1. Field of the Invention

Microorganisms which are capable of producing metabolic products and proteins are becoming increasingly important in industry in such diverse fields as production of industrial chemicals, dairy products, antibiotics and in industrial applications.

Microorganisms can be obtained by routine screening of soil samples; by classical genetic manipulation techniques, e.g., ultraviolet irradiation and mutation selection; or by recombinant DNA technology involving the transfer of genetic material from one microorganism into a host microorganism to alter the genetic characteristics of the host microorganism.

In each case, a series of microorganisms must be screened in order to detect a microorganism which has the desired characteristic. Such screening and isolation of microorganisms usually involves growing and examining a large number of colonies of microorganisms and is labor intensive and time-consuming.

2. Description of the Prior Art

The detection and isolation of a microorganism having a desired genetic trait or which produces a desired substance involves the steps of growing the microorganism on a suitable agar medium and using some technique for detecting the desired microorganism. The desired microorganism is then removed from colonies of other microorganisms, and isolated.

In some bacterial strains a means for "primary" selection exists, e.g., if the desired microorganism is resistant to a certain antibiotic, the microorganisms to be examined can be cultured in the presence of such antibiotic and the microorganisms which survive can be selected and isolated. In contrast, some microorganisms do not carry a "primary" selection trait. Such microorganisms must be screened and isolated by means of biochemical tests, referred to as "screening" techniques. For example, microorganisms which produce the enzyme alpha($\alpha$)-amylase, can be screened by incorporating starch in an agar medium, growing the microorganisms, contacting the agar with iodine and observing the agar for clear zones, which indicate the presence of starch hydrolysis caused by an $\alpha$-amylase secreting microorganism.

Examination of microorganisms grown in an agar medium involving either a primary selectable trait or a biochemical screening test is laborious and time-consuming by conventional techniques. Standard assays exist which can be applied to a relatively small number of colonies growing on an agar plate.

There is a need for an improved method for detecting a desired microorganism. It is therefore an object of the present invention to provide a rapid and economical means for examining a large number of microorganisms growing in an agar medium and selecting a microorganism producing a desired substance, using a small number of manipulative steps and materials.

SUMMARY OF THE INVENTION

The present invention is directed to a method for detecting and/or isolating a microorganism which produces either a secreted or non-secreted substance.

The method for detecting and isolating a microorganism which produces and secretes a desired substance involves the steps of (a) overlaying a sterile semipermeable membrane on an agar surface in a predetermined orientation with respect to the agar surface, the agar containing a reagent capable of reacting with the desired substance; (b) growing microorganisms on the membrane and allowing the substance to pass into the agar medium while retaining said microorganisms on the membrane; (c) removing the membrane from the surface and maintaining the membrane in a sterile environment; (d) observing a detectable reaction between the substance and the reagent, (e) utilizing the predetermined orientation to identify the location of a microorganism producing the substance; and (f) removing the microorganism from the membrane and isolating the microorganism. Alternatively, the agar need not contain the reagent but can be contacted with a reagent; if the desired product is not detectable by means of reaction between the product and a single reagent, the agar medium can be contacted with a series of reagents and a detectable reaction between the substance and at least one of the reagents observed.

The method for detecting a microorganism which produces but does not secrete a desired substance involves the steps of (a) overlaying a sterile semipermeable membrane on the surface of an agar medium in a predetermined orientation with respect to the agar surface containing a reagent capable of reacting with the desired substance; (b) growing the microorganisms on the membrane; (c) lysing the microorganisms in situ to cause the release of the substance and allowing the substance to pass into the agar medium while retaining the microorganisms on the membrane; (d) removing the membrane from the agar surface; (e) observing a detectable reaction between the substance and reagent; and (f) utilizing the predetermined orientation to detect the microorganism which produces the desired substance. Alternatively, the agar need not contain the reagent but can be contacted with a reagent; if the desired nonsecreted product is not detectable by means of a reaction between the product and a single reagent, the agar medium can be contacted with a series of reagents and a detectable reaction between the substance and at least one of the reagents observed.

DETAILED DESCRIPTION OF THE INVENTION

Depending upon the growth requirements and characteristics of the microorganism involved, a wide range of agar media are suitable for use in the present invention. Suitable media are well known in the art and include Spizizen's minimal salts, tryptose blood agar base and nutrient agar.

Semipermeable membranes which allow diffusion of the substance produced by the microorganism into the agar medium, while at the same time retaining the microorganism, are suitable. For example, a semipermeable membrane having a pore size in the range of about $1 \times 10^{-4}$ microns ($\mu$) to about $0.45\mu$ is suitable. In addition, the semipermeable membrane must be chemically inert to the product produced by the microorganism. Suitable membranes can be made of cellulose, nitrocellulose, derivatized nitrocellulose, cellulose acetate, nylon and copolymers of hexafluoropropylene and tetrafluoroethylene.

ATCC numbers refer to microorganism cultures which are available from the American Type Culture Collection, Rockville, Md. BGSC numbers refer to microorganism cultures which are available from the Bacillus Genetic Stock Center, Ohio State University, Columbus, Ohio.

Substances which are produced by microorganisms include enzymes such as amylases, e.g., $\alpha$-amylase; proteases such as alkaline proteases; cellulases and $\beta$-lactamases. Other substances include products such as antibiotics, for example penicillin, streptomycin and erythromycin. Also included are metabolites such as pyruvic acid, ascorbic acid and immunogenic proteins such as capsid proteins and $\beta$-galactosidase. Said substances are produced by species of Bacillus, Streptomyces, Lactobacillus, Streptococcus and yeast.

Suitable microorganisms which yield the substances referred to above are listed below.

| SUBSTANCE | SOURCE |
| --- | --- |
| $\alpha$-amylase | *Bacillus amyloliquefaciens* H (BGSC 10A2) |
| protease | *Bacillus licheniformis* $\alpha$-amylase (ATCC #27811) |
| $\beta$-galactosidase | *E. coli* K12 (ATCC 10798) |
| cellulase | *Trichoderma viride* (ATCC #32086) |
| $\beta$-lactamase | *Bacillus licheniformis* 749/C (ATCC 25972) |
| pencillin | *Penicillium chrysogenum* (ATCC #9480) |
| erythromycin | *Streptomyces erythreus* (ATCC #11635) |
| ascorbic acid pyruvic acid | *Saccharomyces cerevisiae* (ATCC #7754) |
| methionine (amino acid) | *Saccharomyces cerevisiae* (ATCC #32049) |
| $\phi$29 bacteriophage (capsid protein) | (BGSC 1P19) |
| lactic acid | *Lactobacillus* sp or *Streptococcus* sp |

As illustrated hereinafter, suitable reagents include reagents which are reactive with the desired substance produced by a microorganism and produce a detectable reaction. Such reactions are well known to those skilled in the art. The detectable reaction may be accomplished by the use of a single reagent, preferably incorporated in the agar medium. Alternatively, a series of reagents can be used, one of which reacts with the desired product to produce a detectable reaction. A first reagent can be incorporated in the agar medium and after the substance is allowed to pass into the agar medium, the agar medium is contacted with one or more reagents. Alternatively, after the substance is allowed to pass into the agar medium, the agar medium is contacted with one or more reagents.

Suitable single reagents which can be incorporated into the agar medium include bovine serum albumin and casein, which produce a detectable reaction with protease. A series of reagents includes a system using starch and iodine for $\alpha$-amylase detection; polyvinyl alcohol, $I_2$, KI, sodium tetraborate, and penicillin for detecting $\beta$-lactamase; trichloracetic acid, 4,7-diphenyl-1-10-phenanthroline and ferrous ions for detecting ascorbic acid; and polyvinyl alcohol, $I_2$, KI, sodium tetraborate and $\beta$-lactamase for the detection of penicillin.

EXAMPLE I

DNA from a strain of *B. licheniformis* which produces and secretes $\alpha$-amylase (Amy+) was cloned into a strain of *B. subtilis* (BGSC, Strain 1A289) which did not initially produce or secrete $\alpha$-amylase (Amy−), by recombinant DNA techniques as described in co-pending patent application identified as U.S. Ser. No. 438,544, filed concurrently with the present application and incorporated herein by reference, and the transformants examined for $\alpha$-amylase producing microorganisms as described below.

A *B. subtilis* (BGSC strain 1A289) initially sensitive to chloramphenicol ($Cm^S$), Amy− was used.

The *B. subtilis* cells were transformed by a collection of recombinant plasmid DNA molecules each conferring chloramphenicol resistance ($Cm^R$) and containing a random assortment of foreign DNA fragments or genes. Introduction of such plasmids into *B. subtilis* cells resulted in a population of cells which were $Cm^R$ transformants. The $Cm^R$ transformants were then screened for the ability to produce $\alpha$-amylase (Amy+), resulting from the introduction of the $\alpha$-amylase gene carried by a plasmid. Such a cloning procedure necessitated the screening of approximately $1 \times 10^7$ *B. subtilis* colonies for the Amy+ phenotype.

By conventional means, i.e., screening cells on agar plates without membranes, only 100 colonies or less could be analyzed on each agar plate. Crowding of colonies on the agar surface eliminates viewing the subsequent reactions to detect the desired products. Also, the cells may be killed by the reaction steps.

Use of the membranes enables 10,000 to 10,000,000 colonies to be screened on each agar plate. Removal of the membrane containing the cells renders reactions in the agar easily visible, and preserves the cells in a viable state.

A typical experiment requiring the screening of 1,000,000 colonies would involve manipulation of 10,000 agar plates by conventional techniques. Use of the membrane technique as described hereinafter would allow such a screening to be accomplished with only 10 plates.

An agar medium of Tryptose Blood Agar Base, 0.1 percent casamino acids (Difco Laboratories, Detroit, Mich.) and 5 $\mu$g/ml chloramphenicol, incorporating 1.0 percent (w/v) starch as a reagent for $\alpha$-amylase was prepared. A highly purified suitable starch is a starch designated as being "specific for Diastatis Powder and $\alpha$-amylase determination," available from American Society of Brewing Chemists, Inc., St. Paul, Minn. 55121. A 25 ml portion of the medium was placed on a 100 mm petri dish (plate). The plates can be stored in sealed plastic sleeves at 4° C. for up to 3 weeks with no deleterious effects.

Semipermeable membranes, having a 0.45 μm pore size, were used as follows. A suitable membrane is commercially available from Millipore Corporation, Bedford, Mass., under the trade designation Hybridization Membrane Filter Discs.

Two cuts, approximately 5 mm in length were made at right angles to each other, to serve as orientation marks for positioning the membrane onto the starch agar plates. Ashless filter papers were cut into thin strips (approximately 5 mm×50 mm) and placed between the membranes during sterilization. The stacked membranes were submerged in water in a glass petri dish and autoclaved for 30 minutes at 120° C.

The sterile membranes were overlaid on the agar surface of the starch plates by aseptic transfer with sterile filter forceps. On a plate turntable, a sterile glass rod was used to remove the wrinkles and the air bubbles, which prevent intimate contact between the membrane and the agar surface. The positions of the nicks in the filter were labeled on the bottom of each plate. It is critical to the efficiency of the assay that the starch plates be fresh and free of bubbles to ensure that there is intimate contact of the membrane with all areas of the agar.

Following the procedure for transformation of *B. subtilis* 1A289, referred to hereinbefore, 0.1 ml of cells, containing approximately $1 \times 10^5$ colony-forming units per ml, were plated directly onto the membranes. The plates were incubated at 37° C. for 12–18 hours with the plate right-side up. This time was sufficient to allow any α-amylase produced by the microorganisms to pass through the membrane.

After the incubation period, the membranes were aseptically removed with filter forceps. The membrane was removed and transferred to a sterile petri dish and appropriately labeled.

Each starch-agar plate was held with gloves directly over iodine vapor for 4–7 seconds; the iodine vapor functions as a second reagent. Removal of the membrane allowed examination of the agar for the presence of the α-amylase, without exposing the colonies to iodine which can be lethal to the colonies in high concentrations; then placed on a light source to visualize the detectable reaction between the α-amylase and iodine, which produced clear zones of starch hydrolysis against the blue starch-iodine background. One amylase-producing colony in a field of $1 \times 10^5$ Amy$^-$ colonies was detectable by this technique. The locations of the zones were marked directly on the plate bottom immediately after the plate was iodine-developed. This was necessary because the stain began to fade after 7–15 seconds. In lieu of the iodine vapor step, 2 ml of an aqueous iodine solution (2 percent potassium iodide, 0.2 percent iodine) can be used to visualize the zones. Application of iodine in this manner results in a stain which is retained longer than by the vapor method.

In order to recover the amylase-producing colonies, the membrane containing the Amy$^+$ cells was identified and transferred back to its original starch iodine agar plate, using the nicks in the membrane to reorient and achieve proper alignment. By holding the plate over a light source, the labeled zones could be seen through the filter and correlated with a colony on the filter.

The colony was removed from the filter by scraping with a sterile toothpick and suspending the cells in 1.0 ml of broth Tryptose Beef Broth (TBB): 1 percent tryptose, 0.3 percent beef extract, 0.5 percent NaCl, and 0.1 percent casamino acids. Serial dilutions were made and 0.1 ml of cells was plated onto filters over TBAB+-starch+chloramphenicol plates as before. The filter detection assay, described above, was repeated until it was established that a pure culture of Amy$^+$, Cm$^R$ *B. subtilis* cells had been obtained. By this method one clone which produced amylase was detected and isolated from a total of approximately $1 \times 10^7$ colonies which were analyzed.

The detection method of the present invention was utilized in the following Example to detect microorganisms which produce the enzyme beta (β)-lactamase present in a population of cells which do not produce β-lactamase.

EXAMPLE II

*Bacillus licheniformis* 749/C (BGSC) is a strain which produces and excretes β-lactamase. *Bacillus subtilis* A12 (BGSC) is an asporogenic strain which does not produce β-lactamase.

Both microorganisms were grown at 37° C. in a broth consisting of 10 g/L of tryptone (Difco Laboratories, Detroit, Mich.), 5 g/L of yeast extract (Difco), 5 g/L of NaCl and 4 g/L of glucose. *B. licheniformis* 749/C was grown to a concentration of approximately $1 \times 10^7$ cells/ml and *B. subtilis* A12 was grown to approximately $1 \times 10^8$ cells/ml Cell concentrations were determined by plating suitable dilutions on agar plates containing Tryptose Blood Agar Base (Difco), 0.1 percent casamino acids (Difco) and 0.75 percent polyvinyl alcohol (Sigma Chemical Co., St. Louis, Mo.).

Semipermeable membranes were prepared as described in Example I. Sets of 100 mm petri dishes containing 25 ml each of Tryptose Blood Agar Base, 0.1 percent casamino acids and 0.75 percent polyvinyl alcohol (as a first reagent for β-lactamase) were overlaid with sterile semipermeable membrane filters by means of sterile forceps and glass rods to ensure complete contact between the membrane and the agar surface. The positions of the nicks in the filter were marked on the bottom of each plate. Appropriate dilutions of the *B. subtilis* A12 culture were made such that 0.1 ml of the dilutions plated onto the filter surface contained $1 \times 10^5$, $1 \times 10^6$ or $1 \times 10^7$ cells. A set of four plates ot each dilution was prepared. Appropriate dilutions of the *B. licheniformis* 749/C culture were made such that 0.1 ml of the dilutions plated onto the filter surface contained 1, 10, 40 or 100 cells. One of each such dilution was plated onto each of the sets of plates previously spread with the *B. subtilis* A12 cells. The plates were incubated at 37° C. for 12–18 hours with the plate right side up. This time was sufficient to allow any β-lactamase produced by the microorganisms to pass through the membrane.

After the incubation period, the membranes were aseptically removed with filter forceps and transferred to a sterile petri dish and appropriately labeled. Each plate was then flooded with 3-5 ml of a solution containing 0.08 N $I_2$ in 0.32 N KI and 1 percent (w/v) sodium tetraborate for 30-60 seconds; the $I_2$, KI and sodium tetraborate in combination functioned as the second reagent; a dark blue polyvinyl alcohol-iodine complex formed in the agar. The plates were then drained and subsequently flooded with 3-5 ml of a 1 percent (w/v) solution of penicillin G as a third reagent in 0.1 M potassium phosphate buffer, pH 6.8. The plates were placed on a light source to visualize the clear zones that appeared on the dark background. The clear zones were produced by the hydrolysis of penicillin G by β-lactamase in the agar. Zones were counted and marked. It was possible to detect one β-lactamase producing colony among a background of $1 \times 10^7$ colonies per plate which did not produce β-lactamase The detection method of the present invention can be utilized as described in the following Example to detect and isolate microorganisms which produce a protease enzyme present in a population of microorganisms which do not produce protease.

EXAMPLE III

*B. subtilis* SR22 (BGSC strain 1S10) is a microorganism which does not produce protease. *B. amyloliquifaciens* H (BGSC strain 10A2) is a microorganism which produces protease An agar medium of 1.0 percent Bacto-Nutrient agar (Difco) is prepared and while still liquid is mixed with a sterile solution of a non-fat instant dry milk (as a reagent) equilibrated to pH 8.0 with "tris" such that the final medium was 2.5 percent w/v dry milk. A suitable instant dry milk is available from Gallo-way-West Co., Fond du lac, Wisconsin under the trade designation Peake. A 25 ml portion of the medium is poured into each petri plate.

Sterile semipermeable membranes are prepared, marked and positioned on the surface of the agar plates, as described in Example I.

A 0.1 ml volume of a suspension containing $1 \times 10^4$ *B. subtilis* S22 cells and $1 \times 10$ *B. amyloliquifaciens* H cells are plated directly onto the filters. The plates are incubated 48 hours at 37° C. right-side up. After the incubation period, which is sufficient to allow any protease produced by the microorganisms to pass through the membrane, the membranes are aseptically removed, transferred, and labelled, as described in Example 1.

The agar plates are then examined by direct visual inspection for clear zones in the cloudy background of coagulated milk protein in the agar. The clear zones are indicative of hydrolysis of milk protein (casein) by a reaction between the protease produced and secreted by the *B. amyloliquefaciens* H microorganism and the reagent present in the agar.

The *B. amyloliquefaciens* protease-producing microorganisms are isolated from the membrane as described in Example 1.

Substrates for protease other than casein can be incorporated in the agar medium as a reagent. One such substrate is bovine serum albumin (BSA Fraction V, Miles Laboratories, Inc., Elkhart, Ind.). After growth of the microorganisms, the agar containing BSA as a reagent is treated with a solution of 3 percent v/v acetic acid to visualize the zones of hydrolysis. [See *Biochemica et Biophysica Acta*, 580:339-355 (1979)].

The following procedure can be used for the detection of yeast or other microorganisms which produce and secrete ascorbic acid present in a population of microorganisms which do not produce and excrete ascorbic acid.

EXAMPLE IV

Baker's yeast, *Saccharomyces cerevisiae* ATCC 7754 is a yeast strain which produces and excretes ascorbic acid.

The strain is grown in a suitable nutrient broth to a concentration of about $1 \times 10^7$ or $1 \times 10^8$ cells/ml.

Semipermeable membranes are prepared as described in Example I. Sets of 100 mm petri dishes containing 25 ml each of Tryptose Blood Agar Base and 0.1 percent casamino acids are prepared. The agar plates are overlaid with a semipermeable membrane as described in Example I, and appropriate dilutions of the *Saccharomyces cerevisiae* are made such that 0.1 ml of the dilutions plated onto the membrane surface contain from $1 \times 10^5$ to $1 \times 10^7$ cells.

The plates are incubated for about 12-18 hours at 37° C. with the plate right side up, to allow any ascorbic acid produced by the microorganisms to pass through the membrane.

After the incubation period, the membranes are removed as described in Example I. Each plate is flooded with the following series of reagents: 4.0 ml of 5.0 percent trichloroacetic acid; 2.0 ml of ethanol, 1.0 ml of 0.4 percent phosphoric acid in ethanol; 2.0 ml of 0.5 percent 4,7-diphenyl-1,10-phenanthroline in ethanol and 1.0 ml of 0.03 percent $FeCl_3$ in ethanol.

The plates are incubated at 30° C. and placed on a light source to visualize formation of a red colored chelate between the ferrous ions and the phenanthroline, indicating the presence of ascorbic acid. The ascorbic acid-producing colonies can be removed and isolated as described in Example I.

A test to detect and isolate microorganisms which produce and excrete penicillin present in a population of microorganisms which do not produce and excrete penicillin, can be carried out based on the β-lactamase procedure described in Example II.

EXAMPLE V

*Penicillium crysogenum*, ATCC 9480, is grown in a suitable agar nutrient broth to a concentration of about $1 \times 10^8$ cells/ml.

Semipermeable membranes are prepared as described in Example I. Sets of 100 mm petri dishes containing 25 ml each of Tryptose Blood Agar Base and 0.1 percent casamino acids are prepared and 0.75 percent polyvinyl alcohol as a first reagent.

The plates are then incubated as described in Example II to allow any penicillin produced by the microorganisms to pass through the membrane.

The semipermeable membrane is then removed and transferred to a sterile petri dish and appropriately labeled. Each plate is then flooded with a solution of 0.80 N $I_2$, 0.32 N KI and 1 percent sodium tetraborate which functions as a second reagent and the formation of a dark blue polyvinyl alcohol-iodine complex observed. The plates are drained and subsequently flooded with a solution of β-lactamase. The plates are placed on a light source to visualize the clear zones that appeared on the dark background due to the hydrolysis of penicillin by the β-lactamase.

The penicillin-producing colonies can be removed and isolated from the membrane as described in Example I.

The method of the present invention can be used to detect an *E. coli* microorganism which produces β-galactosidase present in a population of microorganisms which do not produce β-galactosidase. In this case, the basis of the detection assay is that the enzyme β-galactosidase also functions as an immunogenic protein.

EXAMPLE VI

A bank of β-galactosidase-deficient (lac⁻) *E. coli* cells, [See *Methods in Enzymology*, 68:432 (1979)] containing plasmids which carry a random assortment of mouse genes, is prepared according to standard recombinant DNA techniques. By means of recombinant DNA techniques, a small number of β-galactosidase producing organisms can be produced resulting from the cloning of the mouse gene for β-galactosidase.

The agar medium consists of 0.5 percent NaCl, 0.4 percent casamino acids, 10 μg/ml thymine, and 1.5 percent Bacto-Agar (Difco). While the agar medium is still molten (45° C.) an appropriate amount of purified or crude antiserum specific for β-galactosidase is added as a reagent. Protocols for the preparation of antiserum and determination of the concentration needed for the assay can be found in *Methods in Enzymology*, 68:430–431, 435–436, and 437–438. The medium is then poured into 100 mm plastic petri plates in a quantity of 12 ml per plate to form a thin layer.

Sterile semipermeable membranes are prepared, marked and positioned on the surface of the plates as described in Example I.

The *E. coli* cells are spread on the membranes, and incubated at 37° C. for 24 hours. Following growth of the cells, the covers of the plates are removed, and the plates are inverted over a source of chloroform or toluene vapor to lyse the colonies on the membranes. Alternatively, the plate can be sprayed with a fine mist of toluene or chloroform. The plates are then left under a fume hood to allow evaporation of residual chloroform or toluene. After approximately 4 hours, during which time the β-galactosidase has diffused through the membrane into the agar plate, the membranes are removed, labeled and saved.

The agar plates are then inspected over a light source for cloudy areas of precipitin formation, indicating the presence of β-galactosidase in a complex with the antibody present in the agar. The appropriate membrane is reoriented on the agar surface and the location of the β-galactosidase-producing colony is thus established.

Detection of the β-galactosidase in the agar plate can also be accomplished by overlaying the agar surface with 2 ml of a solution consisting of 0.6 percent agar and 80 μg/ml 5-bromo-4-chloro-3-indolyl-β, d-galactoside (XG), (Bachem, Marina Del Ray, Calif.), followed by incubation at 37° C. for 90 minutes. The XG acts as a substrate for β-galactosidase and will form a blue zone upon hydrolysis by the enzyme.

Living cells of the appropriate *E. coli* colony, identified by the above procedure, can be recovered from a replicate set of plates, prepared with the same orientation as the assayed set, which have not been exposed to chloroform or toluene.

As indicated earlier the method of the present invention can be used with other substances which are themselves immunogenic or can be rendered immunogenic by coupling to a suitable hapten.

What is claimed is:

1. A method for detecting, identifying and isolating a microorganism which produces a non-secreted desired substance which comprises the steps of:
   (a) overlaying a sterile semipermeable membrane on the surface of an agar medium in a predetermined orientation with respect to said agar surface, said agar containing a reagent capable of reacting with said substance produced by a microorganism but not secreted by said microorganism;
   (b) inoculating said membrane with an inoculum containing said microorganism and growing said microorganism on said membrane by incubating from 12 to 48 hours;
   (c) lysing said microorganism while on said membrane to cause release of said substance and allowing said substance to pass into said agar medium;
   (d) removing said membrane from said agar medium;
   (e) observing a detectable reaction between said substance and said reagent;
   (f) utilizing said predetermined orientation to identify, from a replicate set of plates, the location of said microorganism producing said substance; and
   (g) isolating therefrom said microorganism.

2. A method for detecting, identifying and isolating a microorganism which produce a non-secreted desired substance which comprises the steps of:
   (a) overlaying a sterile semipermeable membrane on the surface of an agar medium in a predetermined orientation with respect to said agar surface;
   (b) inoculating said membrane with an inoculum containing a microorganism and growing said microorganism on said membrane by incubating from 12 to 48 hours;
   (c) lysing said microorganism while on said membrane to cause release of said substance and allowing said substance to pass into said agar medium;
   (d) removing said membrane from said agar medium;
   (e) contacting said agar with one or more reagents and observing a detectable reaction between said substance and at least one of said reagents;
   (f) utilizing said predetermined orientation to identify, from a replicate set of plates, the location of said microorganism producing said substance; and
   (g) isolating therefrom said microorganism.

3. A method as claimed in claim 1 wherein said microorganism is *E. coli*.

4. A method as claimed in claim 2 wherein said microorganism is *E. coli*.

* * * * *